US005861274A

United States Patent [19]
Evans et al.

[11] Patent Number: 5,861,274
[45] Date of Patent: Jan. 19, 1999

[54] NUCLEIC ACIDS ENCODING PEROXISOME PROLIFERATOR-ACTIVATED RECEPTOR

[75] Inventors: Ronald M. Evans; Barry M. Forman, both of La Jolla; Steven A. Kliewer, San Diego; Estelita S. Ong, San Diego; Bruce Blumberg, San Diego, all of Calif.

[73] Assignee: The Salk Institute for Biological Studies, La Jolla, Calif.

[21] Appl. No.: 484,200

[22] Filed: Jun. 7, 1995

Related U.S. Application Data

[63] Continuation-in-part of Ser. No. 270,643, Jul. 1, 1994, abandoned, which is a continuation-in-part of Ser. No. 907,908, Jul. 2, 1992, abandoned, which is a continuation-in-part of Ser. No. 497,935, Mar. 22, 1990, abandoned.

[51] Int. Cl.$^6$ .......................... C12N 15/12; C12N 15/79; C12N 15/85

[52] U.S. Cl. ........................ 435/69.1; 435/325; 435/364; 435/320.1; 536/23.5

[58] Field of Search .......................... 435/6, 69.1, 240.2, 435/252.3, 320.1, 325, 364; 536/23.5; 935/55, 70

[56] References Cited

U.S. PATENT DOCUMENTS

| | | | |
|---|---|---|---|
| 4,981,784 | 1/1991 | Evans et al. | 435/6 |
| 5,071,773 | 12/1991 | Evans et al. | 435/501 |
| 5,091,518 | 2/1992 | Sucov et al. | 536/27 |
| 5,260,432 | 11/1993 | Takaku et al. | 536/235 |
| 5,401,830 | 3/1995 | McKenzie | 530/371 |

FOREIGN PATENT DOCUMENTS

| | | |
|---|---|---|
| 0 244 221 | 4/1987 | European Pat. Off. . |
| WO 91/14695 | 10/1991 | WIPO . |
| WO 91/17253 | 11/1991 | WIPO . |

OTHER PUBLICATIONS

Arriza et al., "The Neuronal Mineralocorticoid Receptor as a Mediator of Glucocoritcoid Response" *Neuron* 1:887–900 (1988).

Bahouth et al., "Immunological Approaches for Probing Receptor Structure and Function" *Trends Pharmacol Sci.* 12:338–343 (1991).

Bardot et al., "PPAR–RXR Hereodimer Activates a Peroxisome Proliferator Element Upstream of the Bifunctional Enzyme Gene" *Biochem. Biophys. Res. Comm.* 192:37–45 (1993).

Beck et al., "The Ontogeny of Peroxisome–Proliferator–Activated Receptor Gene Expression in the Mouse and Rat" *Proc. R. Soc. Lond.* 247:83–87 (1992).

Black and Russo, "Stereological Analysis of the Guinea Pig Adrenal: Effects of Dexamethasone and ACTH Treatment With Emphasis on the Inner Cortex" *Amer. J. Anatomy* 159:85–120 (1980).

Blumberg et al., "Multiple Retinoid–Responsive Receptors in a Simple Cell: Families of Retinoid X Receptors and Retinoic Acid Receptors in the Xenopus Egg" *Proc. Natl. Acad. Sci. USA* 89:2321–2325 (1992).

Bossy et al., "Conservation of Neural Nicotinic Acetylcholine Receptors from Drosophila to Vertebrate Central Nervous Systems" *EMBO Journal* 7:611–618 (1988).

Dreyer et al., "Control of the Peroxisomal β–Oxidation Pathway by a Novel Family of Nuclear Hormone Receptors" *Cell* 68:879–887 (1992).

Evans, R.E. "The Steroid and Thyroid Hormone Receptor Superfamily" *Science* 240:889–895 (1988).

Forman et al., "A Domain Containing Leucine–Zipper–Like Motifs Mediate Novel in vivo Interactions Between the Thyroid Hormone and Retinoic Acid Receptors" *Molecular Endocrinology* 3:1610–1626 (1989).

Forman and Samuels, "Interactions Among a Subfamily of Nuclear Hormone Receptors: The Regulatory Zipper Model" *Mol. Endocrinol.* 4:1293–1301 (1990).

Foxworthy and Eacho, "Effect of the Peroxisome Proliferator LY17883 on Triglyceride Accumulation in Rats Fed a Fat–Free Diet" *Biochem. Pharmacology* 42:1487–1491 (1991).

Gearing et al., "Interaction of the Peroxisome–Proliferator–Activiated Receptor and Retinoid X Receptor" *Proc. Natl. Acad. Sci. USA* 90:1440–1444 (1993).

Gottlicher et al., "Fatty Acids Activate A Chimera of the Clofibric Acid–Activated Receptor and the Glucocorticoid Receptor" *Proc. Natl. Acad. Sci. USA* 89:4653–4657 (1992).

Green and Chambon, "Nuclear Receptors Enhance our Understanding of Transcription Regulation" *Trends in Genetics* 4:309–314 (1988).

Hermans–Borgmeyer al., "Primary Structure of a Developmentally Regulated Nicotinic Acetylcholine Receptor Protein from Drosophila" *EMBO Journal*, 5:1503–1508 (1986).

Heyman et al., "9–Cis Retinoic Acid is a High Affinity Ligand for the Retinoid X Receptor" *Cell* 68:397–406 (1992).

Isseman and Green, "Activation of a Memeber of the Steroid Hormone Receptor Superfamily by Peroxisome Proliferators" *Nature* 347:645–650 (1990).

(List continued on next page.)

*Primary Examiner*—Paula K. Hutzell
*Assistant Examiner*—Robert C. Hayes
*Attorney, Agent, or Firm*—Gray Cary Ware & Freidenrich; Stephen E. Reiter; Gregory P. Raymer

[57] ABSTRACT

Novel peroxisome proliferator-activated receptor subunits designated PPARγ and PPARδ are described. Nucleic acid sequences encoding the receptor subunits, expression vectors containing such sequences and host cells transformed with such vectors are also disclosed, as are heterodimeric PPAR receptors comprising at least one of the invention subunits, and methods for the expression of such novel receptors, and various uses therefor.

7 Claims, 4 Drawing Sheets

OTHER PUBLICATIONS

Keller et al., "Fatty Acids and Retinoids Control Lipid Metabolism Through Activation of Peroxisome Proliferator–Activated Receptor–Retinoid X Receptor Heterodimers" *Proc. Natl. Acad. Sci. USA* 90:2160–2164 (1993).

Kliewer et al., "Convergence of 9–cis Retinoic Acid and Peroxisome Proliferator Signalling Pathways Through Heterodimer Formation of Their Receptors" *Nature* 358:771–774 (1992).

Kliewer et al., "Retinoid Receptor Interacts with Nuclear Receptors in Retinoic Acid, Thyroid Hormone and Vitamin $D_3$ Signalling" *Nature* 355:446–449 (1992).

Ladias and Karathanasis, "Regulation of the Apolipoprotein AI Gene by ARP–1, a Novel Member of the Steroid Receptor Superfamily" *Science* 251:561–565 (1991).

Law et al., "Identification of a New Brain–Specific Transcription Factor, NURR 1" *Mol. Endo* 6(12):2129–2135 (1992).

Lazarow and Fujiki, "Biogenesis of Peroxisomes" *Ann. Rev. Cell Biol.* 1:489–530 (1985).

Levin et al., "9–Cis Retinoic Acid Stereoisomer Binds and Activates the Nuclear Receptor RXRα" *Nature* 355:359–361 (1992).

Mangelsdorf et al., "Nuclear Receptor that Identifies a Novel Retinoic Acid Response Pathway" *Nature* 345:224–229 (1990).

Marcus et al., "Diverse Peroxisome Proliferator–Activated Receptors Bind to the Peroxisome Proliferator–Responsive Elements of the Rat Hydratase/Dehydrogenase and Fatty Acyl–CoA Oxidase Genes but Differentially Induce Expression" *Proc. Natl. Acad. Sci. USA* 90(12):5723–5727 (1993).

Miyajima et al., "Identification of Two Novel Members of erbA Superfamily by Molecular Cloning: The Gene Products of the Two are Highly Similar" *Nucleic Acids Research* 16:11057–11074 (1988).

Mlodzik et al., "The Drosophila seven–up Gene, a Member of the Steroid Receptor Gene Superfamily, Controls Photoreceptor Cell Fates" *Cell* 60:211–224 (1990).

Muerhoff et al., "The Peroxisome Proliferator–Activated Receptor Mediates the Induction of CYP4A6, a Cytochrome P450 Fatty Acid w–Hydroxylase, by Chlofibric Acid" *J. Biol. Chem.* 267:19051–19053 (1992).

Nauber et al., "Abdominal Segmentaion of the Drosophila Embryo Require a Hormone Receptor–like Protein encoded by the Gap Gene knirps" *Nature* 336:489–492 (1988).

Nemali et al., "Comparison of Constitutive and Inducible Levels of Expression of Peroxisomal β–Oxidation and Catalase Genes in Liver and Extrahepatic Tissues of Rat" *Cancer Res.* 48:5316–5324 (1988).

Oro et al., "Relationship Between the Product of the *Drosophila Ultraspiracle* Locus and the Vertebrate Retionoid X Receptor" *Nature* 347:298–301 (1990).

Petruzzelli et al., "Isolation of a Drosophila Genomic Sequence Homologous to the Kinase Domain of the Human Insulin Receptor and Detection of the Phosphorylated Drosophila Receptor with an Anti–Peptide Antibody" *Proc. Natl. Acad. Sci. USA* 83:4710–4714 (1986).

Reddy and Lalwai, "Carcinogenesis by Hepatic Peroxisome Proliferators: Evaluation of the Risk of Hypolipidemic Drugs and Industrial Plasticizers to Humans" *Crit. Rev. Toxicol.* 12:1–58 (1983).

Schmidt et al., "Identification of a New Member of the Steroid Hormone Receptor Superfamily that is Activated by a Peroxisome Proliferator and Fatty Acids" *Mol. Endo.* 6:1634–1641 (1992).

Sher et al., "cDNA Cloning, Chromosomal Mapping, and Functional Characterization of the Human Peroxisome Proliferator Activated Receptor" *Biochemistry* 32:5598–5604 (1993).

Sladek et al., "Liver–Enriched Transcription Factor HNF–4 is a Novel Member of the Steroid Hormone Receptor Superfamily" *Genes & Development* 4:2353–2365 (1990).

Tsia et al., "Molecular Interactions of Steroid Hormone Receptor with its Enhancer Element: Evidence for Receptor Dimer Formation" *Cell* 55:361–369 (1988).

Tugwood et al., "The Mouse Peroxisome Proliferator Activated Receptor Recognizes a Response Element in the 5' Flanking Sequence of the Rat Acyl CoA Oxidase Gene" *EMBO J.* 11:433–439 (1992).

Umesono et al., "Direct Repeats as Selective Response Elements for the Thyroid Hormone, Retinoic Acid, and Vitamin $D_3$ Receptors" *Cell* 65:1255–1266 (1991).

Vamacq and Draye, "Pathophysiology of Peroxisomal β–Oxidation" *Essays Biochem.* 24:115–225 (1989).

Vaughan et al., "Detection and Purification of Inhibin Using Antisera Generated Against Synthetic Peptide Fragments" *Methods in Enzymology* 168:588–617 (1989).

Wadsworth et al., "A Drosophila Genomic Sequence with Homology to Human Epidermal Growth Factor Receptor" *Nature*, 314:178–180 (1985).

Wang et al., "COUP Transcription Factor is a Member of the Steroid Receptor Superfamily" *Nature* 340:163–166 (1989).

Wigler et al., "DNA–Mediated Transfer of the Adenine Phosphoribosyltransferase Locus into Mammalian Cells" *Proc. Natl. Acad. Sci. USA* 76:1373–1376 (1979).

Yao et al., "Functional Ecdysone Receptor is the Product of EcR and Ultraspiracle Genes" *Nature* 366:476–479 (1993).

Zhang et al., "Retinoid X Receptor is an Auxiliary Protein for Thyroid Hormone and Retinoic Acid Receptors" *Nature* 355:441–446 (1992).

Zhu et al. J Biol. Chem. 268 (1993) 26817–26820.

Tontonoz et al. Gene and Development 8 (May 15, 1994) 1224–1234.

Chen et al. Biochem. Biophys. Res. Comm. 196 (1993) 671–677.

Schmidt et al. Molec. Endocrinology 6 (1992) 1634–1641.

Chenet et al./GenBank Sequence Accession #U01665 (1993).

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 2005 base pairs
( B ) TYPE: nucleic acid
( C ) STRANDEDNESS: both
( D ) TOPOLOGY: linear ( i i ) MOLECULE TYPE: cDNA ( i x ) FEATURE:
( A ) NAME/KEY: CDS
( B ) LOCATION: 352..1776

( x i ) SEQUENCE DESCRIPTION: SEQ ID NO:1:

```
ATCGAATCCC  GCGCCCCAGG  CGCTGCCGCT  CTGAGTGCGA  CGGGCCCCGC  CTGGCCGGCC      60

GGAGGACGCG  GAAGAAGAGA  CCTGGGGCGC  TGCCTGGGGT  ATTGGGTCGC  GCGCAGTGAG     120

GGGACCGAGT  GTGACGACAA  GGTGACCGGG  CTGAGGGGAC  GGGCTGAGGA  GAAGTCACAC     180

TCTGACAGGA  GCCTGTGAGA  CCAACAGCCT  GACGGGGTCT  CGGTTGAGGG  GACGCGGGCT     240

GAGAAGTCAC  GTTCTGACAG  GACTGTGTGA  CAGACAAGAT  TTGAAGAAG  CGGTGAACCA      300

CTGATATTCA  GGACATTTTT  AAAAACAAGA  CTACCCTTTA  CTGAAATTAC  C  ATG  GTT    357
                                                              Met  Val
                                                                1
```

| | | | | | | | | | | | | | | | |
|---|---|---|---|---|---|---|---|---|---|---|---|---|---|---|---|
| GAC | ACA | GAG | ATG | CCA | TTC | TGG | CCC | ACC | AAC | TTC | GGA | ATC | AGC | TCT | GTG | 405
| Asp | Thr | Glu | Met | Pro | Phe | Trp | Pro | Thr | Asn | Phe | Gly | Ile | Ser | Ser | Val |
|  |  | 5 |  |  |  |  | 10 |  |  |  |  | 15 |  |  |  |
| GAC | CTC | TCC | GTG | ATG | GAA | GAC | CAC | TCG | CAT | TCC | TTT | GAC | ATC | AAG | CCC | 453
| Asp | Leu | Ser | Val | Met | Glu | Asp | His | Ser | His | Ser | Phe | Asp | Ile | Lys | Pro |
|  |  | 20 |  |  |  |  | 25 |  |  |  |  | 30 |  |  |  |
| TTT | ACC | ACA | GTT | GAT | TTC | TCC | AGC | ATT | TCT | GCT | CCA | CAC | TAT | GAA | GAC | 501
| Phe | Thr | Thr | Val | Asp | Phe | Ser | Ser | Ile | Ser | Ala | Pro | His | Tyr | Glu | Asp |
| 35 |  |  |  |  | 40 |  |  |  |  | 45 |  |  |  |  | 50 |
| ATT | CCA | TTC | ACA | AGA | GCT | GAC | CCA | ATG | GTT | GCT | GAT | TAC | AAA | TAT | GAC | 549
| Ile | Pro | Phe | Thr | Arg | Ala | Asp | Pro | Met | Val | Ala | Asp | Tyr | Lys | Tyr | Asp |
|  |  |  |  | 55 |  |  |  |  | 60 |  |  |  |  | 65 |  |
| CTG | AAG | CTC | CAA | GAA | TAC | CAA | AGT | GCG | ATC | AAA | GTA | GAA | CCT | GCA | TCT | 597
| Leu | Lys | Leu | Gln | Glu | Tyr | Gln | Ser | Ala | Ile | Lys | Val | Glu | Pro | Ala | Ser |
|  |  |  | 70 |  |  |  |  | 75 |  |  |  |  | 80 |  |  |
| CCA | CCT | TAT | TAT | TCT | GAA | AAG | ACC | CAG | CTC | TAC | AAC | AGG | CCT | CAT | GAA | 645
| Pro | Pro | Tyr | Tyr | Ser | Glu | Lys | Thr | Gln | Leu | Tyr | Asn | Arg | Pro | His | Glu |
|  |  | 85 |  |  |  |  | 90 |  |  |  |  | 95 |  |  |  |
| GAA | CCT | TCT | AAC | TCC | CTC | ATG | GCC | ATT | GAG | TGC | CGA | GTC | TGT | GGG | GAT | 693
| Glu | Pro | Ser | Asn | Ser | Leu | Met | Ala | Ile | Glu | Cys | Arg | Val | Cys | Gly | Asp |
|  |  | 100 |  |  |  |  | 105 |  |  |  |  | 110 |  |  |  |
| AAA | GCA | TCA | GGC | TTC | CAC | TAT | GGA | GTT | CAT | GCT | TGT | GAA | GGA | TGC | AAG | 741
| Lys | Ala | Ser | Gly | Phe | His | Tyr | Gly | Val | His | Ala | Cys | Glu | Gly | Cys | Lys |
| 115 |  |  |  |  | 120 |  |  |  |  | 125 |  |  |  |  | 130 |
| GGT | TTT | TTC | CGA | AGA | ACC | ATC | CGA | TTG | AAG | CTT | ATT | TAT | GAT | AGG | TGT | 789
| Gly | Phe | Phe | Arg | Arg | Thr | Ile | Arg | Leu | Lys | Leu | Ile | Tyr | Asp | Arg | Cys |
|  |  |  |  | 135 |  |  |  |  | 140 |  |  |  |  | 145 |  |
| GAT | CTT | AAC | TGC | CGG | ATC | CAC | AAA | AAA | AGT | AGA | AAT | AAA | TGT | CAG | TAC | 837
| Asp | Leu | Asn | Cys | Arg | Ile | His | Lys | Lys | Ser | Arg | Asn | Lys | Cys | Gln | Tyr |
|  |  |  |  | 150 |  |  |  |  | 155 |  |  |  |  | 160 |  |
| TGT | CGG | TTT | CAG | AAG | TGC | CTT | GCT | GTG | GGG | ATG | TCT | CAC | AAT | GCC | ATC | 885
| Cys | Arg | Phe | Gln | Lys | Cys | Leu | Ala | Val | Gly | Met | Ser | His | Asn | Ala | Ile |

```
                       165                            170                               175
AGG  TTT  GGG  CGG  ATG  CCA  CAG  GCC  GAG  AAG  GAG  AAG  CTG  TTG  GCG  GAG              933
Arg  Phe  Gly  Arg  Met  Pro  Gln  Ala  Glu  Lys  Glu  Lys  Leu  Leu  Ala  Glu
     180                      185                      190

ATC  TCC  AGT  GAT  ATC  GAC  CAG  CTG  AAC  CCA  GAG  TCT  GCT  GAT  CTG  CGA              981
Ile  Ser  Ser  Asp  Ile  Asp  Gln  Leu  Asn  Pro  Glu  Ser  Ala  Asp  Leu  Arg
195                      200                      205                      210

GCC  CTG  GCA  AAG  CAT  TTG  TAT  GAC  TCA  TAC  ATA  AAG  TCC  TTC  CCG  CTG             1029
Ala  Leu  Ala  Lys  His  Leu  Tyr  Asp  Ser  Tyr  Ile  Lys  Ser  Phe  Pro  Leu
               215                      220                      225

ACC  AAA  GCC  AAG  GCG  AGG  GCG  ATC  TTG  ACA  GGA  AAG  ACA  ACG  GAC  AAA             1077
Thr  Lys  Ala  Lys  Ala  Arg  Ala  Ile  Leu  Thr  Gly  Lys  Thr  Thr  Asp  Lys
               230                      235                      240

TCA  CCA  TTT  GTC  ATC  TAC  GAC  ATG  AAT  TCC  TTA  ATG  ATG  GGA  GAA  GAT             1125
Ser  Pro  Phe  Val  Ile  Tyr  Asp  Met  Asn  Ser  Leu  Met  Met  Gly  Glu  Asp
          245                      250                      255

AAA  ATC  AAG  TTC  AAA  CAT  ATC  ACC  CCC  CTG  CAG  GAG  CAG  AGC  AAA  GAG             1173
Lys  Ile  Lys  Phe  Lys  His  Ile  Thr  Pro  Leu  Gln  Glu  Gln  Ser  Lys  Glu
     260                      265                      270

GTG  GCC  ATC  CGA  ATT  TTT  CAA  GGG  TGC  CAG  TTT  CGA  TCC  GTA  GAA  GCC             1221
Val  Ala  Ile  Arg  Ile  Phe  Gln  Gly  Cys  Gln  Phe  Arg  Ser  Val  Glu  Ala
275                      280                      285                      290

GTG  CAA  GAG  ATC  ACA  GAG  TAT  GCC  AAA  AAT  ATC  CCT  GGT  TTC  ATT  AAC             1269
Val  Gln  Glu  Ile  Thr  Glu  Tyr  Ala  Lys  Asn  Ile  Pro  Gly  Phe  Ile  Asn
               295                      300                      305

CTT  GAT  TTG  AAT  GAC  CAA  GTG  ACT  CTG  CTC  AAG  TAT  GGT  GTC  CAT  GAG             1317
Leu  Asp  Leu  Asn  Asp  Gln  Val  Thr  Leu  Leu  Lys  Tyr  Gly  Val  His  Glu
               310                      315                      320

ATC  ATC  TAC  ACG  ATG  CTG  GCC  TCC  CTG  ATG  AAT  AAA  GAT  GGA  GTC  CTC             1365
Ile  Ile  Tyr  Thr  Met  Leu  Ala  Ser  Leu  Met  Asn  Lys  Asp  Gly  Val  Leu
          325                      330                      335

ATC  TCA  GAG  GGC  CAA  GGA  TTC  ATG  ACC  AGG  GAG  TTC  CTC  AAA  AGC  CTG             1413
Ile  Ser  Glu  Gly  Gln  Gly  Phe  Met  Thr  Arg  Glu  Phe  Leu  Lys  Ser  Leu
     340                      345                      350

CGG  AAG  CCC  TTT  GGT  GAC  TTT  ATG  GAG  CCT  AAG  TTT  GAG  TTT  GCT  GTG             1461
Arg  Lys  Pro  Phe  Gly  Asp  Phe  Met  Glu  Pro  Lys  Phe  Glu  Phe  Ala  Val
355                      360                      365                      370

AAG  TTC  AAT  GCA  CTG  GAA  TTA  GAT  GAC  AGT  GAC  TTG  GCT  ATA  TTT  ATA             1509
Lys  Phe  Asn  Ala  Leu  Glu  Leu  Asp  Asp  Ser  Asp  Leu  Ala  Ile  Phe  Ile
               375                      380                      385

GCT  GTC  ATT  ATT  CTC  AGT  GGA  GAC  CGC  CCA  GGC  TTG  CTG  AAC  GTG  AAG             1557
Ala  Val  Ile  Ile  Leu  Ser  Gly  Asp  Arg  Pro  Gly  Leu  Leu  Asn  Val  Lys
               390                      395                      400

CCC  ATC  GAG  GAC  ATC  CAA  GAC  AAC  CTG  CTG  CAG  GCC  CTG  GAA  CTG  CAG             1605
Pro  Ile  Glu  Asp  Ile  Gln  Asp  Asn  Leu  Leu  Gln  Ala  Leu  Glu  Leu  Gln
          405                      410                      415

CTC  AAG  CTG  AAT  CAC  CCA  GAG  TCC  TCT  CAG  CTG  TTC  GCC  AAG  GTG  CTC             1653
Leu  Lys  Leu  Asn  His  Pro  Glu  Ser  Ser  Gln  Leu  Phe  Ala  Lys  Val  Leu
     420                      425                      430

CAG  AAG  ATG  ACA  GAC  CTC  AGG  CAG  ATC  GTC  ACA  GAG  CAC  GTG  CAG  CTA             1701
Gln  Lys  Met  Thr  Asp  Leu  Arg  Gln  Ile  Val  Thr  Glu  His  Val  Gln  Leu
435                      440                      445                      450

CTG  CAT  GTG  ATC  AAG  AAG  ACA  GAG  ACA  GAC  ATG  AGC  CTT  CAC  CCC  CTG             1749
Leu  His  Val  Ile  Lys  Lys  Thr  Glu  Thr  Asp  Met  Ser  Leu  His  Pro  Leu
               455                      460                      465

CTC  CAG  GAG  ATC  TAC  AAG  GAC  TTG  TAT  TAGCAGGAAA  GTCCCACCCG                         1796
Leu  Gln  Glu  Ile  Tyr  Lys  Asp  Leu  Tyr
               470                      475

CTGACAACGT  GTTCCTTCTA  TTGATTGCAC  TATTATTTTG  AGGGAAAAAA  ATCTGACACC                      1856
```

```
TAAGAAATTT    ACTGTGAAAA    AGCATTTAAA    AACAAAAAGT    TTTAGAACAT    GATCTATTTT        1916

ATGCATATTG    TTTATAAAGA    TACATTTACA    ATTTACTTTT    AATATTAAAA    ATTACCACAT        1976

TATAAAAAAA    AAAAAAAAAA    AGGAATTCC                                                  2005
```

( 2 ) INFORMATION FOR SEQ ID NO:2:

( i ) SEQUENCE CHARACTERISTICS:
        ( A ) LENGTH: 475 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Val  Asp  Thr  Glu  Met  Pro  Phe  Trp  Pro  Thr  Asn  Phe  Gly  Ile  Ser
 1                    5                   10                            15

Ser  Val  Asp  Leu  Ser  Val  Met  Glu  Asp  His  Ser  His  Ser  Phe  Asp  Ile
               20                   25                       30

Lys  Pro  Phe  Thr  Thr  Val  Asp  Phe  Ser  Ser  Ile  Ser  Ala  Pro  His  Tyr
          35                        40                  45

Glu  Asp  Ile  Pro  Phe  Thr  Arg  Ala  Asp  Pro  Met  Val  Ala  Asp  Tyr  Lys
     50                        55                  60

Tyr  Asp  Leu  Lys  Leu  Gln  Glu  Tyr  Gln  Ser  Ala  Ile  Lys  Val  Glu  Pro
 65                   70                        75                            80

Ala  Ser  Pro  Pro  Tyr  Tyr  Ser  Glu  Lys  Thr  Gln  Leu  Tyr  Asn  Arg  Pro
                85                        90                        95

His  Glu  Glu  Pro  Ser  Asn  Ser  Leu  Met  Ala  Ile  Glu  Cys  Arg  Val  Cys
               100                      105                     110

Gly  Asp  Lys  Ala  Ser  Gly  Phe  His  Tyr  Gly  Val  His  Ala  Cys  Glu  Gly
          115                       120                     125

Cys  Lys  Gly  Phe  Phe  Arg  Arg  Thr  Ile  Arg  Leu  Lys  Leu  Ile  Tyr  Asp
     130                       135                      140

Arg  Cys  Asp  Leu  Asn  Cys  Arg  Ile  His  Lys  Lys  Ser  Arg  Asn  Lys  Cys
145                      150                      155                           160

Gln  Tyr  Cys  Arg  Phe  Gln  Lys  Cys  Leu  Ala  Val  Gly  Met  Ser  His  Asn
                    165                      170                     175

Ala  Ile  Arg  Phe  Gly  Arg  Met  Pro  Gln  Ala  Glu  Lys  Glu  Lys  Leu  Leu
               180                      185                     190

Ala  Glu  Ile  Ser  Ser  Asp  Ile  Asp  Gln  Leu  Asn  Pro  Glu  Ser  Ala  Asp
          195                      200                     205

Leu  Arg  Ala  Leu  Ala  Lys  His  Leu  Tyr  Asp  Ser  Tyr  Ile  Lys  Ser  Phe
     210                       215                      220

Pro  Leu  Thr  Lys  Ala  Lys  Ala  Arg  Ala  Ile  Leu  Thr  Gly  Lys  Thr  Thr
225                      230                      235                           240

Asp  Lys  Ser  Pro  Phe  Val  Ile  Tyr  Asp  Met  Asn  Ser  Leu  Met  Met  Gly
                    245                      250                     255

Glu  Asp  Lys  Ile  Lys  Phe  Lys  His  Ile  Thr  Pro  Leu  Gln  Glu  Gln  Ser
               260                      265                     270

Lys  Glu  Val  Ala  Ile  Arg  Ile  Phe  Gln  Gly  Cys  Gln  Phe  Arg  Ser  Val
          275                      280                      285

Glu  Ala  Val  Gln  Glu  Ile  Thr  Glu  Tyr  Ala  Lys  Asn  Ile  Pro  Gly  Phe
     290                       295                      300

Ile  Asn  Leu  Asp  Leu  Asn  Asp  Gln  Val  Thr  Leu  Leu  Lys  Tyr  Gly  Val
305                      310                      315                           320

His  Glu  Ile  Ile  Tyr  Thr  Met  Leu  Ala  Ser  Leu  Met  Asn  Lys  Asp  Gly
                    325                      330                     335
```

```
Val  Leu  Ile  Ser  Glu  Gly  Gln  Gly  Phe  Met  Thr  Arg  Glu  Phe  Leu  Lys
               340                      345                     350

Ser  Leu  Arg  Lys  Pro  Phe  Gly  Asp  Phe  Met  Glu  Pro  Lys  Phe  Glu  Phe
          355                      360                     365

Ala  Val  Lys  Phe  Asn  Ala  Leu  Glu  Leu  Asp  Asp  Ser  Asp  Leu  Ala  Ile
     370                      375                     380

Phe  Ile  Ala  Val  Ile  Ile  Leu  Ser  Gly  Asp  Arg  Pro  Gly  Leu  Leu  Asn
385                      390                     395                          400

Val  Lys  Pro  Ile  Glu  Asp  Ile  Gln  Asp  Asn  Leu  Leu  Gln  Ala  Leu  Glu
               405                      410                     415

Leu  Gln  Leu  Lys  Leu  Asn  His  Pro  Glu  Ser  Ser  Gln  Leu  Phe  Ala  Lys
               420                      425                     430

Val  Leu  Gln  Lys  Met  Thr  Asp  Leu  Arg  Gln  Ile  Val  Thr  Glu  His  Val
               435                      440                     445

Gln  Leu  Leu  His  Val  Ile  Lys  Lys  Thr  Glu  Thr  Asp  Met  Ser  Leu  His
     450                      455                     460

Pro  Leu  Leu  Gln  Glu  Ile  Tyr  Lys  Asp  Leu  Tyr
465                      470                     475
```

( 2 ) INFORMATION FOR SEQ ID NO:3:

( i ) SEQUENCE CHARACTERISTICS:
( A ) LENGTH: 2012 base pairs
( B ) TYPE: nucleic acid
( C ) STRANDEDNESS: both
( D ) TOPOLOGY: linear ( i i ) MOLECULE TYPE: cDNA ( i x ) FEATURE:
( A ) NAME/KEY: CDS
( B ) LOCATION: 263..1582

( x i ) SEQUENCE DESCRIPTION: SEQ ID NO:3:

```
GAATTCCCTG  GGGATTAATG  GGAAAAGTTT  TGGCAGGAGC  TGGGGGATTC  TGCGGAGCCT      60

GCGGGACGGC  GGCAGCGGCG  CGAGAGGCGG  CCGGGACAGT  GCTGTGCAGC  GGTGTGGGTA     120

TGCGCATGGG  ACTCACTCAG  AGGCTCCTGC  TCACTGACAG  ATGAAGACAA  ACCCACGGTA     180

AAGGCAGTCC  ATCTGCGCTC  AGACCCAGAT  GGTGGCAGAG  CTATGACCAG  GCCTGCAGCG     240

CCACGCCAAG  TGGGGGTCAG  TC ATG GAA CAG CCA CAG GAG GAG ACC CCT GAG         292
              Met Glu Gln Pro Gln Glu Glu Thr Pro Glu
               1               5                  10

GCC CGG GAA GAG GAG AAA GAG GAA GTG GCC ATG GGT GAC GGA GCC CCG            340
Ala Arg Glu Glu Glu Lys Glu Glu Val Ala Met Gly Asp Gly Ala Pro
            15                  20                  25

GAG CTC AAT GGG GGA CCA GAA CAC ACG CTT CCT TCC AGC AGC TGT GCA            388
Glu Leu Asn Gly Gly Pro Glu His Thr Leu Pro Ser Ser Ser Cys Ala
         30                      35                  40

GAC CTC TCC CAG AAT TCC TCC CCT TCC TCC CTG CTG GAC CAG CTG CAG            436
Asp Leu Ser Gln Asn Ser Ser Pro Ser Ser Leu Leu Asp Gln Leu Gln
        45                      50                  55

ATG GGC TGT GAT GGG GCC TCA GGC GGC AGC CTC AAC ATG GAA TGT CGG            484
Met Gly Cys Asp Gly Ala Ser Gly Gly Ser Leu Asn Met Glu Cys Arg
        60                      65                  70

GTG TGC GGG GAC AAG GCC TCG GGC TTC CAC TAC GGG GTC CAC GCG TGC            532
Val Cys Gly Asp Lys Ala Ser Gly Phe His Tyr Gly Val His Ala Cys
75                      80                      85                  90

GAG GGG TGC AAG GGC TTC TTC CGC CGG ACA ATC CGC ATG AAG CTC GAG            580
Glu Gly Cys Lys Gly Phe Phe Arg Arg Thr Ile Arg Met Lys Leu Glu
            95                     100                 105
```

```
TAT GAG AAG TGC GAT CGG ATC TGC AAG ATC CAG AAG AAG AAC CGC AAC     628
Tyr Glu Lys Cys Asp Arg Ile Cys Lys Ile Gln Lys Lys Asn Arg Asn
            110                 115                 120

AAG TGT CAG TAC TGC CGC TTC CAG AAG TGC CTG GCA CTC GGC ATG TCG     676
Lys Cys Gln Tyr Cys Arg Phe Gln Lys Cys Leu Ala Leu Gly Met Ser
        125                 130                 135

CAC AAC GCT ATC CGC TTT GGA CGG ATG CCG GAC GGC GAG AAG AGG AAG     724
His Asn Ala Ile Arg Phe Gly Arg Met Pro Asp Gly Glu Lys Arg Lys
    140                 145                 150

CTG GTG GCG GGG CTG ACT GCC AGC GAG GGG TGC CAG CAC AAC CCC CAG     772
Leu Val Ala Gly Leu Thr Ala Ser Glu Gly Cys Gln His Asn Pro Gln
155                 160                 165                 170

CTG GCC GAC CTG AAG GCC TTC TCT AAG CAC ATC TAC AAC GCC TAC CTG     820
Leu Ala Asp Leu Lys Ala Phe Ser Lys His Ile Tyr Asn Ala Tyr Leu
                175                 180                 185

AAA AAC TTC AAC ATG ACC AAA AAG AAG GCC CGG AGC ATC CTC ACC GGC     868
Lys Asn Phe Asn Met Thr Lys Lys Lys Ala Arg Ser Ile Leu Thr Gly
            190                 195                 200

AAG TCC AGC CAC AAC GCA CCC TTT GTC ATC CAC GAC ATC GAG ACA CTG     916
Lys Ser Ser His Asn Ala Pro Phe Val Ile His Asp Ile Glu Thr Leu
        205                 210                 215

TGG CAG GCA GAG AAG GGC CTG GTG TGG AAA CAG CTG GTG AAC GGG CTG     964
Trp Gln Ala Glu Lys Gly Leu Val Trp Lys Gln Leu Val Asn Gly Leu
    220                 225                 230

CCG CCC TAC AAC GAG ATC AGT GTG CAC GTG TTC TAC CGC TGC CAG TCC    1012
Pro Pro Tyr Asn Glu Ile Ser Val His Val Phe Tyr Arg Cys Gln Ser
235                 240                 245                 250

ACC ACA GTG GAG ACA GTC CGA GAG CTC ACC GAG TTC GCC AAG AAC ATC    1060
Thr Thr Val Glu Thr Val Arg Glu Leu Thr Glu Phe Ala Lys Asn Ile
                255                 260                 265

CCC AAC TTC AGC AGC CTC TTC CTC AAT GAC CAG GTG ACC CTC CTC AAG    1108
Pro Asn Phe Ser Ser Leu Phe Leu Asn Asp Gln Val Thr Leu Leu Lys
            270                 275                 280

TAT GGC GTG CAC GAG GCC ATC TTT GCC ATG CTG GCC TCC ATC GTC AAC    1156
Tyr Gly Val His Glu Ala Ile Phe Ala Met Leu Ala Ser Ile Val Asn
        285                 290                 295

AAA GAC GGG CTG CTG GTG GCC AAC GGC AGT GGC TTC GTC ACC CAC GAG    1204
Lys Asp Gly Leu Leu Val Ala Asn Gly Ser Gly Phe Val Thr His Glu
300                 305                 310

TTC TTG CGA AGT CTC CGC AAG CCC TTC AGT GAC ATC ATT GAG CCC AAG    1252
Phe Leu Arg Ser Leu Arg Lys Pro Phe Ser Asp Ile Ile Glu Pro Lys
315                 320                 325                 330

TTC GAG TTT GCT GTC AAG TTC AAT GCG CTG GAG CTC GAT GAC AGT GAC    1300
Phe Glu Phe Ala Val Lys Phe Asn Ala Leu Glu Leu Asp Asp Ser Asp
                335                 340                 345

CTG GCG CTC TTC ATC GCG GCC ATC ATT CTG TGT GGA GAC CGG CCA GGC    1348
Leu Ala Leu Phe Ile Ala Ala Ile Ile Leu Cys Gly Asp Arg Pro Gly
            350                 355                 360

CTC ATG AAT GTG CCC CAG GTA GAA GCC ATC CAG GAC ACC ATT CTG CGG    1396
Leu Met Asn Val Pro Gln Val Glu Ala Ile Gln Asp Thr Ile Leu Arg
        365                 370                 375

GCT CTA GAA TTC CAT CTG CAG GTC AAC CAC CCT GAC AGC CAG TAC CTC    1444
Ala Leu Glu Phe His Leu Gln Val Asn His Pro Asp Ser Gln Tyr Leu
    380                 385                 390

TTC CCC AAG CTG CTG CAG AAG ATG GCA GAC CTG CGG CAG CTG GTC ACT    1492
Phe Pro Lys Leu Leu Gln Lys Met Ala Asp Leu Arg Gln Leu Val Thr
395                 400                 405                 410

GAG CAT GCC CAG ATG ATG CAG TGG CTA AAG AAG ACG GAG AGT GAG ACC    1540
Glu His Ala Gln Met Met Gln Trp Leu Lys Lys Thr Glu Ser Glu Thr
                415                 420                 425
```

```
TTG  CTG  CAC  CCC  CTG  CTC  CAG  GAA  ATC  TAC  AAG  GAC  ATG  TAC              1582
Leu  Leu  His  Pro  Leu  Leu  Gln  Glu  Ile  Tyr  Lys  Asp  Met  Tyr
               430                      435                     440

TAAGGCCGCA  GCCCAGGCCT  CCCCTCAGGC  TCTGCTGGGC  CCAGCCACGG  ACTGTTCAGA          1642

GGACCAGCCA  CAGGCACTGG  CAGTCAAGCA  GCTAGAGCCT  ACTCACAACA  CTCCAGACAC          1702

GTGGCCCAGA  CTCTTCCCCC  AACACCCCCA  CCCCCACCAA  CCCCCCCATT  CCCCCAACCC          1762

CCCTCCCCCA  CCCCGCTCTC  CCCATGGCCC  GTTTCCTGTT  TCTCCTCAGC  ACCTCCTGTT          1822

CTTGCTGTCT  CCCTAGCGCC  CTTGCTCCCC  CCCCTTTGCC  TTCCTTCTCT  AGCATCCCCC          1882

TCCTCCCAGT  CCTCACATTT  GTCTGATTCA  CAGCAGACAG  CCCGTTGGTA  CGCTCACCAG          1942

CAGCCTAAAA  GCAGTGGGCC  TGTGCTGGCC  CAGTCCTGCC  TCTCCTCTCT  ATCCCCTTCA          2002

AAGGGAATTC                                                                       2012
```

( 2 ) INFORMATION FOR SEQ ID NO:4:

( i ) SEQUENCE CHARACTERISTICS:
        ( A ) LENGTH: 440 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Glu  Gln  Pro  Gln  Glu  Glu  Thr  Pro  Glu  Ala  Arg  Glu  Glu  Lys
 1                  5                        10                      15

Glu  Glu  Val  Ala  Met  Gly  Asp  Gly  Ala  Pro  Glu  Leu  Asn  Gly  Gly  Pro
               20                       25                      30

Glu  His  Thr  Leu  Pro  Ser  Ser  Ser  Cys  Ala  Asp  Leu  Ser  Gln  Asn  Ser
               35                       40                      45

Ser  Pro  Ser  Ser  Leu  Leu  Asp  Gln  Leu  Gln  Met  Gly  Cys  Asp  Gly  Ala
      50                      55                      60

Ser  Gly  Gly  Ser  Leu  Asn  Met  Glu  Cys  Arg  Val  Cys  Gly  Asp  Lys  Ala
 65                      70                      75                      80

Ser  Gly  Phe  His  Tyr  Gly  Val  His  Ala  Cys  Glu  Gly  Cys  Lys  Gly  Phe
                    85                       90                      95

Phe  Arg  Arg  Thr  Ile  Arg  Met  Lys  Leu  Glu  Tyr  Glu  Lys  Cys  Asp  Arg
               100                      105                     110

Ile  Cys  Lys  Ile  Gln  Lys  Lys  Asn  Arg  Asn  Lys  Cys  Gln  Tyr  Cys  Arg
          115                      120                     125

Phe  Gln  Lys  Cys  Leu  Ala  Leu  Gly  Met  Ser  His  Asn  Ala  Ile  Arg  Phe
     130                      135                     140

Gly  Arg  Met  Pro  Asp  Gly  Glu  Lys  Arg  Lys  Leu  Val  Ala  Gly  Leu  Thr
145                      150                     155                     160

Ala  Ser  Glu  Gly  Cys  Gln  His  Asn  Pro  Gln  Leu  Ala  Asp  Leu  Lys  Ala
               165                      170                     175

Phe  Ser  Lys  His  Ile  Tyr  Asn  Ala  Tyr  Leu  Lys  Asn  Phe  Asn  Met  Thr
          180                      185                     190

Lys  Lys  Lys  Ala  Arg  Ser  Ile  Leu  Thr  Gly  Lys  Ser  Ser  His  Asn  Ala
          195                      200                     205

Pro  Phe  Val  Ile  His  Asp  Ile  Glu  Thr  Leu  Trp  Gln  Ala  Glu  Lys  Gly
     210                      215                     220

Leu  Val  Trp  Lys  Gln  Leu  Val  Asn  Gly  Leu  Pro  Pro  Tyr  Asn  Glu  Ile
225                      230                     235                     240

Ser  Val  His  Val  Phe  Tyr  Arg  Cys  Gln  Ser  Thr  Thr  Val  Glu  Thr  Val
               245                      250                     255
```

```
Arg  Glu  Leu  Thr  Glu  Phe  Ala  Lys  Asn  Ile  Pro  Asn  Phe  Ser  Ser  Leu
               260                 265                      270

Phe  Leu  Asn  Asp  Gln  Val  Thr  Leu  Leu  Lys  Tyr  Gly  Val  His  Glu  Ala
          275                      280                      285

Ile  Phe  Ala  Met  Leu  Ala  Ser  Ile  Val  Asn  Lys  Asp  Gly  Leu  Leu  Val
     290                      295                300

Ala  Asn  Gly  Ser  Gly  Phe  Val  Thr  His  Glu  Phe  Leu  Arg  Ser  Leu  Arg
305                      310                 315                           320

Lys  Pro  Phe  Ser  Asp  Ile  Ile  Glu  Pro  Lys  Phe  Glu  Phe  Ala  Val  Lys
                    325                      330                      335

Phe  Asn  Ala  Leu  Glu  Leu  Asp  Asp  Ser  Asp  Leu  Ala  Leu  Phe  Ile  Ala
               340                 345                           350

Ala  Ile  Ile  Leu  Cys  Gly  Asp  Arg  Pro  Gly  Leu  Met  Asn  Val  Pro  Gln
     355                      360                      365

Val  Glu  Ala  Ile  Gln  Asp  Thr  Ile  Leu  Arg  Ala  Leu  Glu  Phe  His  Leu
     370                 375                      380

Gln  Val  Asn  His  Pro  Asp  Ser  Gln  Tyr  Leu  Phe  Pro  Lys  Leu  Leu  Gln
385                      390                 395                           400

Lys  Met  Ala  Asp  Leu  Arg  Gln  Leu  Val  Thr  Glu  His  Ala  Gln  Met  Met
               405                      410                           415

Gln  Trp  Leu  Lys  Lys  Thr  Glu  Ser  Glu  Thr  Leu  Leu  His  Pro  Leu  Leu
          420                      425                      430

Gln  Glu  Ile  Tyr  Lys  Asp  Met  Tyr
          435                 440
```

( 2 ) INFORMATION FOR SEQ ID NO:5:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

GGNTTYCAYT AYGGNGTNCA YCG                                               23

( 2 ) INFORMATION FOR SEQ ID NO:6:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Gly  Phe  His  Tyr  Gly  Val  His  Ala
1                   5
```

NUCLEIC ACIDS ENCODING PEROXISOME PROLIFERATOR-ACTIVATED RECEPTOR

RELATED APPLICATIONS

This application is a continuation-in-part of U.S. application Ser. No. 08/270,643, filed Jul. 1, 1994, now abandoned, which is a continuation-in-part of U.S. application Ser. No. 07/907,908, filed Jul. 2, 1992, now abandoned, which is a continuation-in-part of U.S. application Ser. No. 07/497,935, filed Mar. 22, 1990, now abandoned.

FIELD OF INVENTION

The present invention relates to novel members of the steroid/thyroid superfamily of receptors, as well as uses therefor.

BACKGROUND OF THE INVENTION

Peroxisome proliferators are a structurally diverse group of compounds which, when administered to rodents, elicit dramatic increases in the size and number of hepatic and renal peroxisomes, as well as concomitant increases in the capacity of peroxisomes to metabolize fatty acids via increased expression of the enzymes required for the β-oxidation cycle (Lazarow and Fujiki, *Ann. Rev. Cell Biol.* 1:489–530 (1985); Vamecq and Draye, *Essays Biochem.* 24:1115–225 (1989); and Nelali et al., *Cancer Res.* 48:5316–5324 (1988)). Chemicals included in this group are the fibrate class of hypolipidermic drugs, herbicides, and phthalate plasticizers (Reddy and Lalwani, *Crit. Rev. Toxicol.* 12:1–58 (1983)). Peroxisome proliferation can also be elicited by dietary or physiological factors such as a high-fat diet and cold acclimatization.

Insight into the mechanism whereby peroxisome proliferators exert their pleiotropic effects was provided by the identification of a member of the nuclear hormone receptor superfamily activated by these chemicals (Isseman and Green, *Nature* 347-645-650 (1990)). This receptor, termed peroxisome proliferator activated receptor alpha (PPARα), was subsequently shown to be activated by a variety of medium and long-chain fatty acids and to stimulate expression of the genes encoding rat acyl-CoA oxidase and hydratase-dehydrogenase (enzymes required for peroxisomal β-oxidation), as well as rabbit cytochrome P450 4A6, a fatty acid ω-hydroxylase (Gottlicher et al., *Proc. Natl. Acad. Sci. USA* 89:4653–4657 (1992); Tugwood et al., EMPO J. 11:433–439 (1992); Bardot et al., *Biochem. Biophys. Res. Comm.* 192:37–45 (1993); Muerhoff et al., *J. Biol. Chem.* 267:19051–19053 (1992); and Marcus et al., *Proc. Natl. Acad. Sci. USA* 90(12):5723–5727 (1993). The foregoing references support a physiological role for PPARα in the regulation of lipid metabolism. PPARα activates transcription by binding to DNA sequence elements, termed peroxisome proliferator response elements (PPRE), as a heterodimer with the retinoid X receptor. The retinoid X receptor is activated by 9-cis retinoic acid (see Kliewer et al., *Nature* 358:771–774 (1992), Gearing et al., *Proc. Natl. Acad. Sci. USA* 90:1440–1444 (1993), Keller et al., *Proc. Natl. Acad. Sci. USA* 90:2160–2164 (1993), Heyman et al., *Cell* 68:397–406 (1992), and Levin et al., *Nature* 355:359–361 (1992)). Since the PPARα-RXR complex can be activated by peroxisome proliferators and/or 9-cis retinoic acid, the retinoid and fatty acid signaling pathways are seen to converge in modulating lipid metabolism.

BRIEF DESCRIPTION OF THE INVENTION

In accordance with the present invention, there are provided isolated mammalian peroxisome proliferator-activated receptor subunit proteins of the γ and δ subtypes, and functional fragments thereof. In addition, there are provided isolated nucleic acids encoding mammalian peroxisome proliferator-activated receptor subunit proteins, as well as fragments thereof. There are also provided vectors containing the above-described nucleic acids, as well as cells containing such nucleic acids and/or vectors.

The present invention also provides methods for the recombinant production of mammalian peroxisome proliferator-activated receptor proteins comprising at least one PPAR subunit protein of the γ and δ subtype, and functional fragments thereof, as well as methods to identify clones encoding the above-described receptor subunit proteins, and functional fragments thereof.

Also provided by the present invention are methods for screening compounds to determine those which bind to mammalian peroxisome proliferator-activated receptor proteins comprising at least one PPAR subunit protein of the γ or δ subtype, or functional fragments thereof, as well as bioassays for evaluating whether test compounds are agonists or antagonists for receptor proteins of the invention, or functional modified forms of said receptor protein(s).

BRIEF DESCRIPTION OF THE FIGS.

FIG. 1 presents a schematic comparison of the members of the PPAR gene family using mPPARα as a reference. Comparisons among the different domains of the proteins are expressed as percent amino acid identity.

FIG. 2 demonstrates that PPARγ and PPARδ fail 30 to respond to the peroxisome proliferator Wy 14,643. CV-1 cells were cotransfected with reporter plasmid PPRE$_3$-TK-LUC and either no receptor expression plasmid (−), CMX-PPARα, CMX-PPARγ, or CMX-PPARδ and then incubated in either the absence (−) or presence (+) of 5 μM Wy 14,643. Luciferase activities are expressed as percentages of the maximal response where 100% is the activity obtained with PPARα in the presence of 5 μM Wy 14,643.

FIG. 3 illustrates the ability of PPARγ and PPARδ to repress PPARα-mediated responsiveness to Wy 14,643. CV-1 cells were cotransfected with reporter plasmid PPRE$_3$-TK-LUC and either no receptor expression plasmid (NONE) or CMX-PPARα (10 ng) in either the absence or presence of CMX-PPARγ (100 ng) or CMX-PPARδ (100 ng). Cells were then incubated in either the absence (−) or presence (+) of 5 μM Wy 14,643. Luciferase activities are presented as fold-activation relative to cells which were not transfected with receptor expression plasmid and were not treated with Wy 14,643.

FIG. 4 demonstrates that PPAR isoforms are pharmacologically distinct. CV-1 cells were cotransfected with reporter plasmid PPRE$_3$-TK-LUC and either no receptor expression plasmid (−), CMX-PPARα, CMX-PPARγ, or CMX-PPARδ in either the absence or presence of 5 μM Wy 14,643 (WY), 30 μM linoleic acid (C18:2), or 30 μM LY-171883 (LY). Luciferase activities are presented as the fold activation achieved in compound-treated versus mock-treated cells. Similar results were obtained in triplicate in three independent experiments.

DETAILED DESCRIPTION OF THE INVENTION

Figure 1:
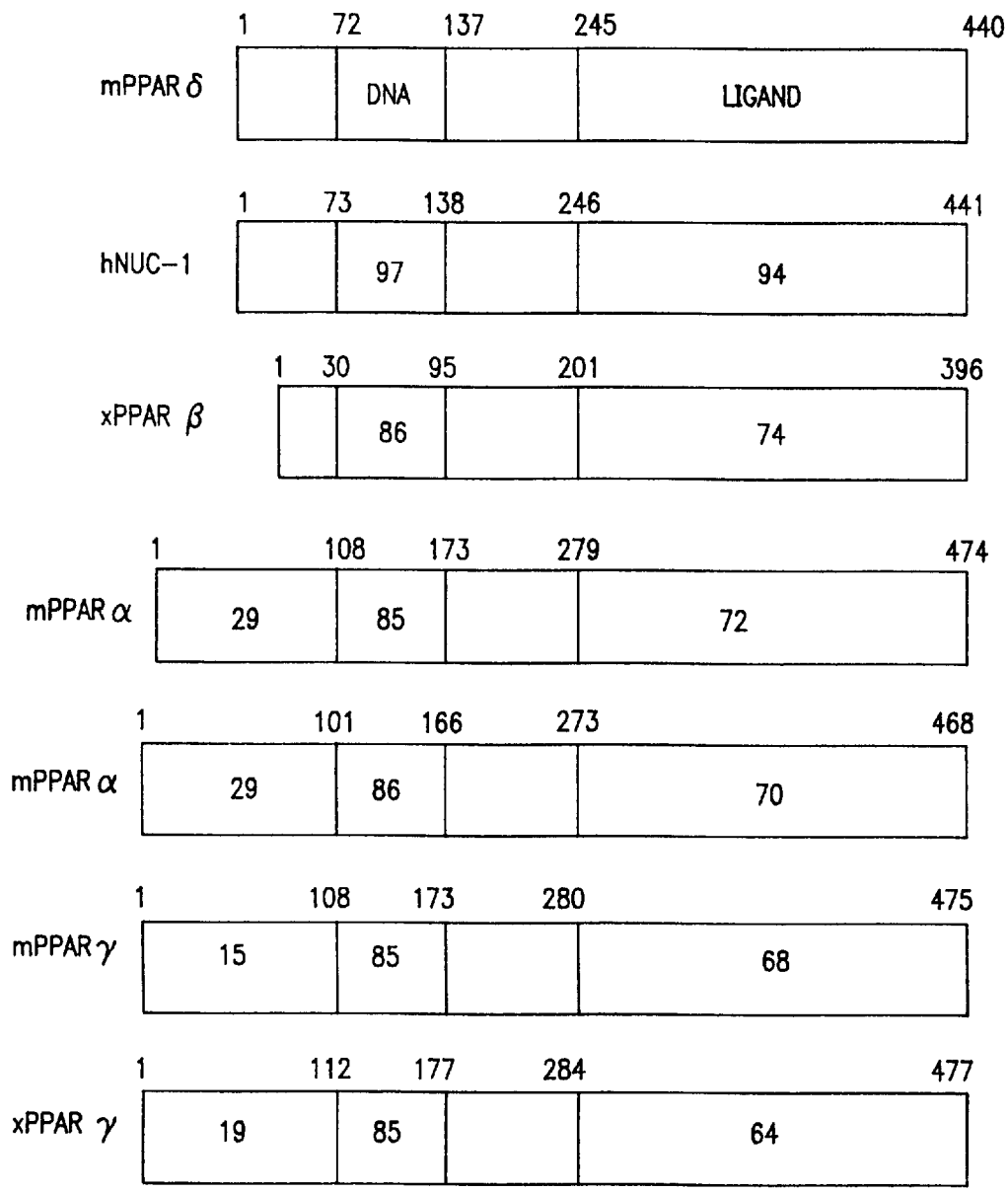

Two novel PPAR receptor subunits have been cloned and characterized. These novel γ and δ isoforms (subunits) together with the α subunit display marked differences in their responsiveness to peroxisome proliferators and fatty acids, as well as differences in their temporal and spatial patterns of expression. These observations suggest a broad role for the PPAR family during development and in adult physiology.

The existence of multiple PPAR isoforms with distinct expression patterns has been found to correlate with the fact that the three isoforms have different ligand specificities. Indeed, the PPAR isoforms are shown herein to be pharmacologically distinct. Thus, PPARα, PPARγ and PPARδ are most efficiently activated by Wy 14,643, LY-171883, and linoleic acid, respectively. Remarkably, Wy 14,643, which results in approximately 100-fold induction in reporter expression in the presence of PPARα, fails to activate either PPARγ or PPARδ.

With regard to this differential responsiveness to activators of peroxisome proliferation, the relationship among the PPAR isoforms may be analogous to that between the glucocorticoid and mineralocorticoid receptors (GR and MR, respectively). While both receptors can bind to the same response element, and both respond to mineralocorticoids and corticosteroids, MR and GR display differential sensitivities to aldosterone and specific glucocorticoids such as dexamethasone, respectively (Arriza et al., *Neuron* 1:887–900 (1988)) . Thus, the ratio of these receptors to their ligands provides a means of determining tissue-specific expression of target genes. Similarly, the existence of multiple PPAR isoforms with overlapping ligand specificities may provide the means for tissue-specific regulation of gene expression by peroxisome proliferators and fatty acids.

In addition to their differential responsiveness to peroxisome proliferators, the three PPAR isoforms also display distinct yet overlapping expression patterns. As previously shown, PPARα mRNA is abundant in liver and kidney (Isseman and Green, supra; Beck et al., *Proc. R. Soc. Lond.* 247:83–87 (1992)), tissues in which peroxisome proliferators result in dramatic increases in the numbers of peroxisomes and concomitant increases in peroxisomal β-oxidation (Nemali et al., supra) . In contrast, the levels of PPARγ mRNA and PPARδ mRNA, which can act as dominant repressors of PPARα-mediated responsiveness to Wy 14,643, are low in these tissues. Thus, a pattern emerges in which tissues that are most responsive to peroxisome proliferators such as Wy 14,643 are observed to express high amounts of PPARα mRNA and relatively low amounts of PPARγ mRNA and PPARδ mRNA. These data suggest that the ratio of the PPAR isoforms is likely to play a critical role in establishing the degree of responsiveness of tissues to specific peroxisome proliferators.

Widespread expression of PPARδ is observed in both the embryo and in adult tissues. This observation suggests that this isoform may play a general "housekeeping" role. In contrast, PPARγ is observed to be expressed almost exclusively in the adrenal and spleen. The expression of all three PPAR isoforms in the adrenal is particularly intriguing, since diseases which result in peroxisome dysfunction (e.g. adrenoleukodystrophy and Zellweger syndrome) cause gross morphological changes in adrenal cells and, eventually, adrenal deficiency. These observations suggest a critical role for peroxisomes in this tissue (Vamecq and Draye, supra). Interestingly, peroxisomes can be induced to proliferate in hamster adrenals in response to treatment with adrenocorticotropic hormone and corticosteroids (Black and Russo, *Amer. J. Anatomy* 159:85–120 (1980)), indicating the presence of adrenal-specific signaling pathway(s) for peroxisome proliferation. The differential expression of PPARγ in the adrenal suggests that this isoform may respond to an adrenal-enriched ligand.

Accordingly, in accordance with the present invention, there are provided isolated mammalian peroxisome proliferator-activated receptor subunit proteins of the γ or δ subtype and functional fragments thereof.

As employed herein, the phrase "mammalian peroxisome proliferator-activated receptor subunit proteins of the γ or δ subtype" refers to isolated and substantially purified as well as recombinantly produced proteins which are members of the steroid/thyroid superfamily of receptors, and which mediate the pleiotropic effects of peroxisome proliferators (such as medium and long-chain fatty acids). Such receptors participate in the formation of heterodimeric species with retinoid X receptors (RXRs) and comprise an amino-terminal domain, a DNA binding domain, and a ligand binding domain. Also contemplated within this definition are variants thereof encoded by mRNA generated by alternative splicing of a primary transcript.

Use of the terms "recombinantly produced", "isolated" or "substantially pure" in the present specification and claims as a modifier of DNA, RNA, polypeptides or proteins means that the modified substances have been produced by the hand of man, and thus are separated from their native in vivo cellular environment. As a result of this human intervention, the recombinant/isolated/substantially pure DNAs, RNAs, polypeptides and proteins of the invention are useful in ways that the naturally occurring DNAs, RNAs, polypeptides or proteins are not, for example, in assays to identify selective drugs or compounds.

The novel receptors of the present invention also can be included as part of a panel of receptors which are screened to determine the selectivity of interaction of proposed agonists or antagonists of other steroid hormone receptors. Thus, a compound which is believed to interact selectively, for example, with the glucocorticoid receptor, should not have any substantial effect on any other receptors, including invention receptors. However, if such a proposed compound does interact with the invention receptors, then the probability of side effects caused by the activation of other receptors in addition to the target receptor, is clearly indicated. For example, the use of many drugs in the treatment of hormone-related disorders is currently restricted by side effects caused by the activation of "non-target" receptors. Employment of the invention receptors in a panel of receptors in a screen to determine the selectivity of interaction of potential ligands provides a means to identify receptor-specific ligands that are therapeutically superior than currently used ligands that cause unwanted side effects.

As used herein, the term splice variant refers to variant PPAR encoding nucleic acid(s) produced by differential processing of primary transcript(s) of genomic DNA, resulting in the production of more than one mRNA. cDNA derived from differentially processed primary transcript will encode PPAR receptor proteins that have regions of complete amino acid identity and regions having different amino acid sequences. Thus, the same genomic sequence can lead to the production of multiple, related mRNAs and corresponding proteins. Both the resulting mRNAs and proteins are referred to herein as "splice variants".

Accordingly, also contemplated within the scope of the present invention are nucleic acids that encode mammalian PPAR receptor subunit proteins as defined above, but that by virtue a degenerate genetic code do not necessarily hybridize to the nucleic acids set forth in SEQ ID NOs: 1 or 3 under specific hybridization conditions. Nucleic acid fragments encoding invention receptor subunit proteins are capable of forming a functional heterodimer with one or more RXR receptor protein isoform(s). Typically, unless a PPAR receptor protein is encoded by mRNA that arises from alternative splicing (i.e., a splice variant), PPAR receptor encoding DNA and encoded protein share substantial sequence homology with at least one of the PPAR receptor-encoding DNAs and encoded proteins described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional PPAR receptor protein.

Exemplary nucleic acid sequences encoding mammalian peroxisome proliferator-activated receptor subunit proteins of the γ subtype are represented by nucleotide sequences which encode substantially the same amino acid sequence as set forth in SEQ ID NO:2. Presently preferred sequences encode the same amino acid sequence as set forth in SEQ ID NO:2.

Exemplary nucleic acid sequences can alternatively be characterized as those nucleotide sequences which encode mammalian peroxisome proliferator-activated receptor subunit proteins of the γ subtype and hybridize under high stringency conditions to SEQ ID NO:1.

Exemplary nucleic acid sequences encoding mammalian peroxisome proliferator-activated receptor subunit proteins of the δ subtype are represented by nucleotides which encode substantially the same amino acid sequence as set forth in SEQ ID NO:4. Presently preferred sequences encode the same amino acid sequence as set forth in SEQ ID NO:4.

Especially preferred sequences are those which have substantially the same nucleotide sequence as that set forth in SEQ ID NO:1.

Exemplary nucleic acid sequences can alternatively be characterized as those nucleotide sequences which encode mammalian peroxisome proliferator-activated receptor subunit proteins of the δ subtype and hybridize under high stringency conditions to SEQ ID NO:3.

Especially preferred nucleic acid sequences are those which have substantially the same nucleotide sequence as the coding sequences in SEQ ID NO:3.

The phrase "stringency of hybridization" is used herein to refer to conditions under which polynucleic acid hybrids are stable. As known to those of skill in the art, the stability is reflected in the melting temperature ($T_m$) of the hybrids. $T_m$ can be approximated by the formula:

$$81.5° C. -16.6(\log_{10}[Na^+]) + 0.41(\% G+C) - 600/1,$$

where 1 is the length of the hybrid in number of nucleotides. $T_m$ decreases approximately 1°–1.5° C. with every 1% decrease in sequence homology. In general, the stability of a hybrid is a function of sodium ion concentration and temperature. Typically, the hybridization reaction is initially performed under conditions of low stringency, followed by washes of varying, but higher, stringency. Reference to hybridization stringency relates to such washing conditions. Thus, as used herein:

(1) HIGH STRINGENCY refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.;

(2) MODERATE STRINGENCY refers to conditions that permit hybridization in 50% formamide, 5× Denhart's solution, 5× SSPE, 0.2% SDS at 42° C., followed by washing in 0.2× SSPE, 0.2% SDS, at 65° C.; and (3) LOW STRINGENCY refers to conditions that permit hybridization in 10% formamide, 5× Denhart's solution, 6× SSPE, 0.2% SDS at 42° C., followed by washing in 1× SSPE, 0.2% SDS, at 50° C.

It is understood that these conditions may be varied using a variety of buffers and temperatures well known to skilled artisans.

As used herein, the phrase "substantial sequence homology" refers to nucleotide sequences which share at least about 90% identity, and amino acid sequences which typically share more than 95% amino acid identity. It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

As used herein, the phrase "substantially the same" refers to nucleotide sequences, ribonucleotide sequences, or amino acid sequences, that have slight and non-consequential sequence variations from the actual sequences disclosed herein. Species that are "substantially the same" are considered to be equivalent to the disclosed sequences, and as such are within the scope of the appended claims. In this regard, "slight and non-consequential sequence variations" mean that sequences that are substantially the same as invention sequences disclosed and claimed herein, are functionally equivalent to the sequences disclosed and claimed herein. Functionally equivalent sequences will function in substantially the same manner to produce substantially the same results as the nucleic acid and amino acid sequences disclosed and claimed herein. Specifically, functionally equivalent nucleic acids encode proteins that have conservative amino acid variations, such as substitution of a non-polar residue for another non-polar residue or a charged residue for a similarly charged residue. These changes are recognized by those of skill in the art as modifications that do not substantially alter the tertiary structure of the protein.

Fragments of invention nucleic acid sequences are useful as hybridization probes, wherein such fragments comprise at least 14 contiguous nucleotides of the above-described nucleic acids, and wherein the fragment is labeled with a detectable substituent. Suitable detectable substituents can be readily determined by those of skill in the art, and include such species as radiolabeled molecules, fluorescent molecules, enzymes, ligands, and the like.

As used herein, a probe is single- or double-stranded DNA or RNA that has a sequence of nucleotides that includes at least 14 contiguous bases that are the same as (or the complement of) any 14 or more contiguous bases set forth in SEQ ID NOs:1 or 3. Preferred regions for the construction of probes include those regions predicted to encode a DNA binding domain. Such regions are preferred because they are most highly conserved among members of the steroid/thyroid superfamily of receptors.

As a particular application of the invention sequences, genetic screening can be carried out using the nucleic acid sequences of the invention as probes. Thus, nucleic acid samples from patients having conditions suspected of involving alteration/modification of any one or more of the PPAR receptor subtypes can be screened with appropriate probes to determine if abnormalities exist with respect to the endogenous PPAR receptor proteins.

In accordance with yet another embodiment of the present invention, there are provided vectors comprising nucleic acid sequences, as well as cells and vectors containing such sequences. Such host cells, including bacterial, yeast and mammalian cells can be used for expressing invention nucleic acids to produce PPAR receptor protein(s). Incorporation of cloned DNA into a suitable expression vector, transfection of eukaryotic cells with a plasmid vector or a combination of plasmid vectors, each encoding one or more distinct genes, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection by $CaPO_4$ precipitation with a vector encoding the heterologous DNA (see, e.g., Wigler et al. (1979) *Proc. Natl. Acad. Sci.* 76:1373–1376), DEAE-dextran, electroporation, microinjection, or lipofectamine (GIBCO BRL #18324-012). Transfected host cells can then be cultured under conditions whereby the receptor subunit protein(s) encoded by the DNA is (are) recombinantly expressed.

The present invention further provides a mammalian peroxisome proliferator-activated receptor, expressed recombinantly in a host cell. The receptor comprises at least one PPAR subunit, wherein the PPAR subunit is PPARγ or PPARδ, and at least one retinoid X receptor isoform. The invention receptor has the ability to repress PPARα-mediated responses activated by Wy 14,643, Also provided by the present invention are mammalian peroxisome proliferator-activated subunit proteins, expressed recombinantly in a host cell wherein the receptor subunits have substantially the same amino acid sequence as set forth in SEQ ID NOs: 2 or 4.

In accordance with still another embodiment of the present invention, there is provided a method for the recombinant production of mammalian peroxisome proliferator-activated receptor proteins comprising at least one PPAR subunit of the γ or δ subtype, or functional fragments thereof. Such method comprises expressing the above-described nucleic acid(s) in a suitable host cell.

In accordance with still another embodiment of the present invention, there is provided a method to identify clones encoding mammalian peroxisome proliferator-activated receptor subunit proteins of the γ or δ subtype, or functional fragments thereof. Such method comprises screening a genomic or cDNA library with an invention nucleic acid probe under low stringency hybridization conditions, and identifying those clones which display a substantial degree of hybridization to said fragment.

Nucleic acids encoding mammalian peroxisome proliferator-activated receptor subunit protein of the γ or δ subtype, or functional fragments thereof may be isolated by screening suitable human cDNA or human genomic libraries under suitable hybridization conditions with nucleic acids disclosed herein (including nucleotide sequences derived from SEQ ID NOs:1 or 3). Suitable libraries can be prepared from appropriate tissue samples, e.g., brain tissue, heart tissue, intestinal tissue, kidney tissue, liver tissue, spleen tissue, and the like. The library can be screened with nucleic acid including substantially the entire receptor-encoding sequence thereof, or the library may be screened with a suitable probe, as described above.

After screening the library, positive clones are identified by means of a hybridization signal; the identified clones are characterized by restriction enzyme mapping and/or DNA sequence analysis, and then examined, by comparison with the sequences set forth herein to ascertain whether they encode a complete PPAR receptor subunit protein (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and encoded proteins provided herein.

The ligand-binding domain (LBD) of nuclear hormone receptors is a complex multifunctional unit containing subdomains for dimerization, transcriptional suppression and hormone-induced transactivation (Forman and Samuels, *Mol. Endocrinol.* 4:1293–1301 (1990)). The dimerization domain includes a series of heptad repeats flanked by sequences required for ligand binding. Thus, the dimerization domain is embedded within the larger LBD. This structural arrangement raises the possibility that dimerization may serve as an allosteric modulator of ligand binding and transactivation. It has previously been shown that the Drosophila ecdysone receptor (EcR) acquires ligand binding activity after heterodimerization with USP (Drosophila homolog of RXR; see Yao et al., in *Nature* 366:476–479 (1993)). Thus, differential interactions among receptor LBDs can either restrict, redirect or lead to an acquisition of new ligand binding phenotypes.

It has recently been shown that PPARα binds to its cognate response elements as a heterodimer with the RXR (see Kliewer et al., supra, Gearing et al., supra, or Keller et al., supra). The resulting PPARα-RXR complex can respond to both peroxisome proliferators and 9-cis retinoic acid (see Kliewer et al., (1992), supra). It has now been found that PPARγ and PPARδ also cooperate with RXR in the formation of heterodimers, and in binding to DNA as heterodimers. Ultimately, the regulation of peroxisome physiology is likely a consequence of a complex interplay among the multiple PPAR and RXR isoforms and the ligands for these receptors.

In accordance with the present invention, there are provided combinations of receptors comprising at least two different members of the steroid/thyroid superfamily of receptors, wherein one receptor is either PPARγ or PPARδ, and wherein said receptors are associated in the form of a multimer, preferably a heterodimer. A particularly preferred combination of receptors is a heterodimer comprising either PPARγ or PPARδ and a subtype of RXR.

Combinations contemplated by the present invention can broadly be referred to as "multimeric species," which is intended to embrace all of the various oligomeric forms in which members of the steroid/thyroid superfamily of receptors (including fragments thereof comprising the dimerization domains thereof) are capable of associating in combination with either PPARγ or PPARδ. Thus, reference to "combinations" of steroid receptors or "multimeric" forms of steroid receptors includes homodimeric combinations of a single PPARγ or PPARδ receptor (including fragments thereof comprising the dimerization domains thereof), heterodimeric combinations of either a PPARγ or PPARδ receptor and another different receptor (including fragments thereof comprising the dimerization domains thereof), homotrimeric combinations of a single PPARγ or PPARδ receptor (including fragments thereof comprising the dimerization domains thereof), heterotrimeric combinations of two or three different receptors including PPARγ or PPARδ (including fragments thereof comprising the dimerization domains thereof), homotetrameric combinations of a single PPARγ or PPARδ receptor (including fragments thereof comprising the dimerization domains thereof), heterotetrameric combinations of two or more different receptors including PPARγ or PPARδ (including fragments thereof comprising the dimerization domains thereof), and the like.

As employed herein, the phrase "members of the steroid/thyroid superfamily of receptors" (also known as "nuclear receptors" or "intracellular receptors") refers to hormone binding proteins that operate as ligand-dependent transcription factors, including identified members of the steroid/thyroid superfamily of receptors for which specific ligands have not yet been identified (referred to hereinafter as "orphan receptors"). These hormone binding proteins have the intrinsic ability to bind to specific DNA sequences. Following binding, the transcriptional activity of target gene (i.e., a gene associated with the specific DNA sequence) is modulated as a function of the ligand bound to the receptor.

The DNA-binding domains of all of these nuclear receptors are related, consisting of 66–68 amino acid residues, and possessing about 20 invariant amino acid residues, including nine cysteines. A member of the superfamily can be identified as a protein which contains the above-mentioned invariant amino acid residues, which are part of the DNA-binding domain of such known steroid receptors as the human glucocorticoid receptor (amino acids 421–486), the estrogen receptor (amino acids 185–250), the mineralocorticoid receptor (amino acids 603–668), the human retinoic acid receptor (amino acids 88–153). The highly conserved amino acids of the DNA-binding domain of members of the superfamily are well-known as set forth, for example in PCT WO 94/01558. Thus, the DNA-binding domain is a minimum of 66 amino acids in length, but can contain several additional residues.

Exemplary members of the steroid/thyroid superfamily of receptors contemplated for use in the practice of the present invention (including the various isoforms thereof) include steroid receptors such as mineralocorticoid receptor, progesterone receptor, androgen receptor, vitamin $D_3$ receptor, and the like; plus retinoid receptors, such as the various isoforms of RAR (e.g., RARα, RARβ, or RARγ), the various isoforms of RXR (e.g., RXRα, RXRβ, or RXRγ), and the like; thyroid receptors, such as TRα, TRβ, and the like; as well as other gene products which, by their structure and properties, are considered to be members of the superfamily, as defined hereinabove, including the various isoforms thereof. Examples of orphan receptors include HNF4 [see, for example, Sladek et al., in *Genes & Development* 4: 2353–2365 (1990)], the COUP family of receptors [see, for example, Miyajima et al., in *Nucleic Acids Research* 16: 11057–11074 (1988), and Wang et al., in *Nature* 340: 163–166 (1989)], COUP-like receptors and COUP homologs, such as those described by Mlodzik et al., in *Cell* 60: 211–224 (1990) and Ladias et al., in *Science* 251: 561–565 (1991), the ultraspiracle receptor [see, for example, Oro et al., in *Nature* 347: 298–301 (1990)], and the like. Presently preferred members of the superfamily for use in the practice of the present invention are the various isoforms of RXR (e.g., RXRα, RXRβ, or RXRγ).

The formation of multimeric (e.g., heterodimeric) species can modulate the ability of the first receptor to trans-activate transcription of genes maintained under expression control in the presence of ligand for said first receptor. The actual effect on activation of transcription (i.e., enhancement or repression of transcription activity) will vary depending on the receptor species which is combined with either a PPARγ or PPARδ receptor to form the multimeric species, as well as on the response element with which the multimeric species interacts.

In accordance with the present invention, there are provided multimeric receptor species which belong to the steroid/thyroid superfamily of receptors, comprising at least the dimerization domain of at two different members of the steroid/thyroid superfamily of receptors, wherein one of the members is selected from the invention PPARγ or PPARδ.

As employed herein, the term "dimerization domain" of a member of the steroid/thyroid superfamily of receptors refers to that portion of the receptor which is believed to be involved in the formation of multimeric receptor species. This domain typically comprises the carboxy-terminal portion of the receptor, i.e., that portion of a receptor which is 3' with respect to the DNA-binding domain of the receptor. See, e.g., Evans, in *Science* 240:889–895 (1988), and Forman and Samuels, *Mol. Endocrinol.* 4:1293–1301 (1990). Presently preferred members of the superfamily for use in deriving the dimerization domain are the various isoforms of RXR (e.g., RXRα, RXRβ, or RXRδ).

In accordance with the present invention, there are also provided heterodimer complexes comprising either PPARγ or PPARδ and a silent partner therefor.

As employed herein, the term "silent partner" refers to members of the steroid/thyroid superfamily of receptors which are capable of forming heterodimeric species with either PPARγ or PPARδ, wherein the silent partner of the heterodimer does not have any ligand bound to the ligand-binding domain (LBD) when the silent partner is complexed with a PPAR subtype (i.e., only the PPAR co-partner of the heterodimer binds ligand). Presently preferred silent partners for use in the practice of the present invention are the various isoforms of RXR (e.g., RXRα, RXRβ, or RXRδ).

In accordance with a further embodiment of the present invention, there is provided a method for screening compounds to determine those which bind to mammalian peroxisome proliferator-activated receptor proteins comprising at least one PPAR subunit of the γ or δ subtype, or functional fragments thereof. Such method comprises employing receptor protein(s) of the invention in a binding assay, which comprises, contacting receptor protein(s) of the invention with test compound, and identifying those compounds which bind to invention receptor protein(s).

In accordance with a still further embodiment of the present invention, there is provided a bioassay for evaluating whether test compounds are agonists for receptor proteins of the invention, or functional modified forms of said receptor protein(s). Such bioassay comprises:

(1) contacting suitable host cells expressing said receptor protein with test compound under physiological conditions, wherein said host cells contain DNA encoding a reporter protein, wherein said DNA is operatively linked to a PPAR-response element;

(2) monitoring said host cells for expression of reporter gene, wherein expression of reporter protein reflects transcriptional activity of the receptor protein and, therefore, the presence of an activated receptor-ligand complex.

In accordance with yet another embodiment of the present invention, there is provided a bioassay for evaluating whether test compounds are antagonists for receptor proteins of the invention, or functional modified forms of said receptor protein(s). Such bioassay comprises:

contacting suitable host cells with
(i) increasing concentrations of at least one compound whose ability to inhibit the transcription activation activity of agonists of mammalian peroxisome proliferator-activated receptor proteins of the γ or δ subtype is sought to be determined, and (ii) a fixed concentration of at least one agonist for said receptor protein(s) or functional modified forms thereof, wherein suitable test cells express mammalian peroxisome proliferator-activated receptor proteins comprising at least one PPAR subunit of the γ or δ subtype and DNA encoding a reporter protein, wherein said DNA is operatively linked to a PPAR-response element; and thereafter assaying for evidence of transcription of said reporter gene in said cells as a function of the concentration of said compound in said culture medium, thereby indicating the ability of said compound to inhibit activation of transcription by agonists of mammalian peroxisome proliferator-activated receptor proteins comprising at least one PPAR subunit of the γ or δ subtype.

In accordance with a still further embodiment of the present invention, there is provided a method for identifying ligands selective for heterodimers comprising either PPARγ or PPARδ and a silent partner therefor. Such method comprises comparing the level of expression of reporter when cells containing a reporter construct, either PPARγ or PPARδ and silent partner therefor are exposed to test compound, relative to the level of expression of reporter when cells containing a reporter construct, either PPARγ or PPARδ and a member of the steroid/thyroid superfamily which is not a silent partner therefor are exposed to test compound, and selecting those compounds which activate only the combination of either PPARγ or PPARδ and silent partner therefor.

In accordance with yet another embodiment of the present invention, there are provided antibodies generated against the invention proteins. Such antibodies can be employed for studying receptor tissue localization, subunit composition, structure of functional domains, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) Trends Pharmacol Sci. vol. 12:338–343; Current Protocols in Molecular Bioloqy (Ausubel et al., eds.) John Wiley and Sons, New York (1989)]. Factors to consider in selecting portions of the invention receptor protein subunit sequences for use as immunogen (as, for example, a synthetic peptide or a recombinantly produced bacterial fusion protein) include antigenicity, accessibility (i.e., internal or external domains), uniqueness to the particular protein subunit, and the like.

The availability of sequence-specific antibodies enables use of immunohistochemical techniques to monitor the distribution and expression density of various protein subunits (e.g., in normal versus diseased brain tissue). Such antibodies can also be employed for diagnostic and therapeutic applications.

In accordance with yet another embodiment of the present invention, there are provided methods for modulating processes mediated by mammalian peroxisome proliferator-activated receptor proteins comprising at least one PPAR subunit of the γ or δ subtype. Such methods comprise contacting mammalian peroxisome proliferator-activated receptor proteins of the γ or δ subtype with an effective, modulating amount of agonist, antagonist or antibody according to the present invention.

The antibodies, agonists and/or antagonists of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc, depending on the mode of administration employed.

Processes which are mediated by mammalian peroxisome proliferator-activated receptor proteins of the γ or δ subtype include, for example, macrophage production in the spleen which is believed to be important in atherosclerosis.

The invention will now be described in greater detail with reference to the following non-limiting examples.

EXAMPLE 1

Screening of CDNA libraries

PPARγ was isolated by screening an adult mouse liver λZAP cDNA library (Stratagene) with a synthetic oligonucleotide (GGNTTYCAYTAYGGNGTNCAYCG; SEQ ID NO:5) under conditions previously described by Blumberg et al., in Proc. Natl. Acad. Sci. USA 89:2321–2325 (1992). This oligonucleotide is a mixture of all possible DNA sequences encoding the amino acid sequence GFHYGVHA (SEQ ID NO:6), a sequence present in the loop of the first zinc finger in the Xenopus PPARα, PPARβ and PPARγ isoforms.

PPARδ was isolated by screening an E6.5 mouse λZAPII cDNA library (a gift of D. E. Weng and J. D. Gerhart, Johns Hopkins University) under low stringency conditions with a cDNA fragment encoding the human retinoic acid receptor αDNA binding domain (Mangelsdorf et al., Nature 345:224–229 (1990)). In both screens, positive clones were converted to plasmids by the automatic excision process.

EXAMPLE 2

Cotransfection Assay

The mammalian expression vectors pCMX-PPARα, pCMX-PPARγ and pCMX-PPARδ were constructed by inserting the cDNA inserts of PPARα, PPARγ, and PPARδ into pCMX as previously described by Umesono et al., in Cell 65:1255–1266 (1991)). Construction of the reporter PPRE₃-TK-LUC has also been previously described by Kliewer et al., (1992) supra. Cotransfection assays in CV-1 cells were done in 48 well plates using N-[1-(2,3-dioleoyloxy)-propyl[N,N,N-trimethyl ammonium methyl sulfate (DOTAP) according to the manufacturer's instructions (Boehringer Mannheim). Transfections contained long of receptor expression plasmid vector, 20 ng of the reporter PPRE₃-TK-LUC, 60 ng of pCMX-βGAL (β-galactosidase) as an internal control, and 210 ng of carrier plasmid pGEM. Cells were incubated in the presence of DOTAP for 8 hours, washed, and incubated in the presence of peroxisome proliferators or fatty acids for 36 hours. Cell extracts were prepared and assayed for luciferase and β-galactosidase activity as previously described (Umesono, supra). All experimental points were done in triplicate.

EXAMPLE 3

Northern Analysis

Preparation of poly(A)⁺ RNA from rat tissues and Northern analysis were performed as previously described (Mangelsdorf et al., supra). Thus, Northern blot analysis of PPAR mRNA was carried out employing adult and embryonic tissue. Adult male rat tissues and mouse embryos from gestation day 10.5 to 18.5 were employed. The exposure time for each of the blots was 48 hours. The sizes of the transcripts, based on RNA size markers, were 8.5 kb (PPARα), 1.9 kb (PPARγ), and 3.5 kb (PPARδ).

EXAMPLE 4

DNA Binding Assays

Gel mobility shift assays were performed as previously described by Kliewer et al. (1992) supra. PPARα, PPARγ, PPARδ, RXRα, RXRβ and RXRγ were synthesized in vitro using the TNT coupled transcription/translation system (Promega) according to the manufacturer's instructions.

EXAMPLE 5

Isolation of three murine PPAR isoforms

The function of peroxisome proliferators has been most extensively studied in rodents, where treatment with these compounds results in marked increases in peroxisome size and number and concomitant increases in the expression of the genes encoding the enzymes of the peroxisomal β-oxidation pathway. To gain insight into the function of PPAR isoforms, mouse embryonic and adult liver libraries were screened for PPARα-related gene products. In addition to PPARα, two types of PPARα-related clones were isolated.

The first clone encodes a 475-amino acid protein that is 56% identical to mouse (m)PPARα and 76% identical to Xenopus (x)PPARγ. Since this clone is 97% and 84% identical to the DNA binding and ligand binding domains of xPPARγ, respectively, it is designated mPPARγ (see SEQ ID NOs:1 and 2).

The second clone encodes a 440-amino acid protein that is closely related to NUC-1 (see SEQ ID NOs:3 and 4, and FIG. 1), a PPARα-related receptor recently isolated from a human osteosarcoma library (see Schmidt et al., in Mol. Endo. 6:1634–1641 (1992)). Since this second clone is not highly homologous to any of the previously identified PPAR isoforms (i.e., mPPARα, xPPARα, xPPARβ or xPPARγ; see FIG. 1), it appears to represent a novel receptor, and is, therefore, designated mPPARδ. Of the approximately 50 positives characterized during the course of screening, no mouse homolog of xPPARβ was identified.

EXAMPLE 6

PPARAα, PPARγ, and PPARδ are differentially expressed in the adult and embryo

The expression patterns of the murine PPAR isoforms were examined in the embryo and adult. Northern analysis of poly(A)+ RNA isolated from adult male rat tissues revealed differential yet overlapping patterns of expression of the three isoforms. Both PPARα and PPARδ are widely expressed, with PPARα message levels highest in the liver, kidney, heart, and adrenal, and PPARδ message highest in the heart, adrenal, and intestine. In contrast, PPARγ displays a more restricted distribution pattern, with abundant expression in only the adrenal and spleen, although message is also detectable in the heart, kidney, and intestine.

The developmental expression of the PPAR isoforms was also examined through Northern analysis of whole mouse embryo RNA. PPARα and PPARγ displayed similar expression patterns during mouse embryogenesis, with message first appearing at day 13.5 postconception and increasing until birth. In contrast, PPARδ message was abundant at all the embryonic time points tested, suggesting a broad role for this isoform during development. Thus, the PPAR isoforms are seen to be differentially expressed in both the embryo and the adult.

EXAMPLE 7

Evidence for pharmacological differences between PPARα, PPARγ and PPARδ

The relatively high degree of conservation within the ligand binding domains of PPARα, PPARγ and PPARδ suggested that these PPAR isoforms might respond to the same activators. Accordingly, each of the PPAR isoforms was first tested for responsiveness to Wy 14,643, a peroxisome proliferator and potent activator of PPARα (Reddy and Lalwani, Crit. Rev. Toxicol. 12:1–58 (1983) ). Cotransfection of PPARα expression plasmid resulted in a dramatic (>100-fold) increase in activation of a reporter construct containing three copies of the acyl-CoA oxidase PPRE (AOX-PPRE) upstream of the thymidine kinase promoter driving luciferase expression (PPRE$_3$-TK-LUC) in response to Wy 14,643 (FIG. 2).

Figure 2:
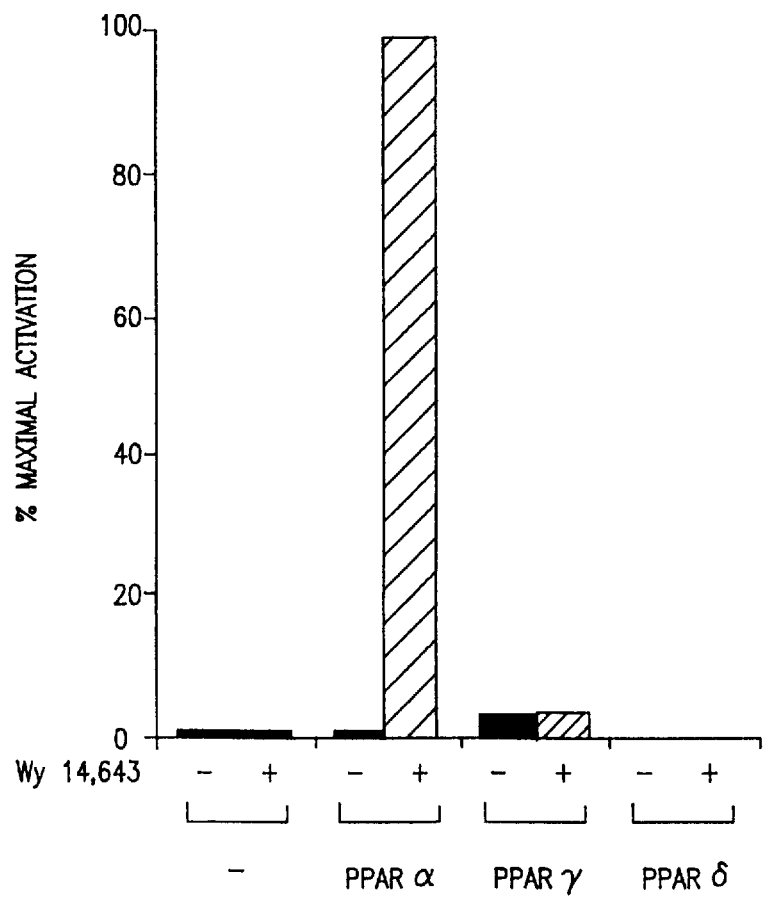
Figure 3:
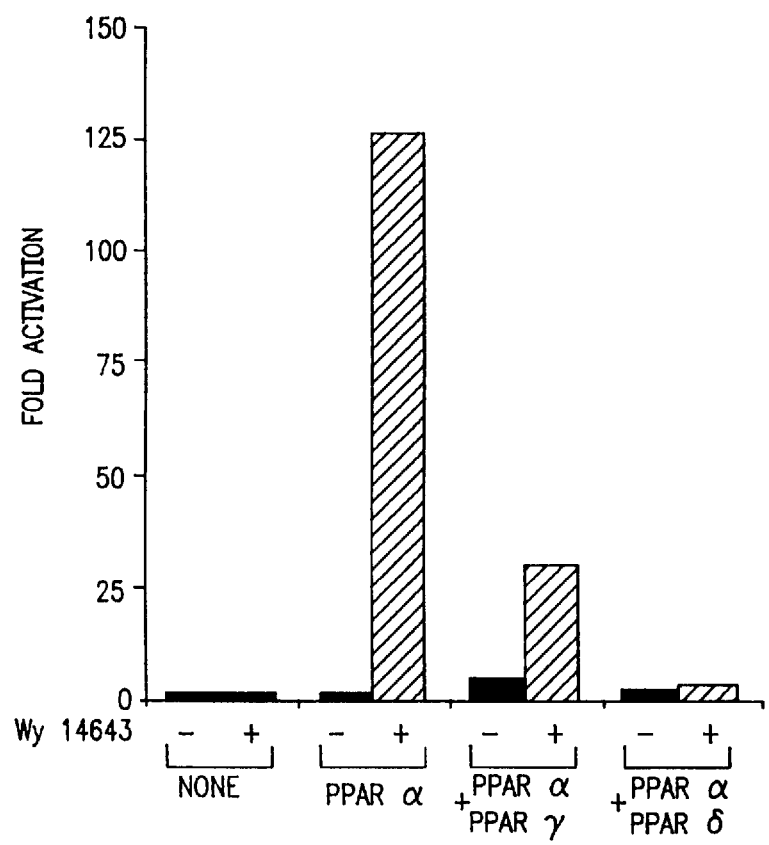

In contrast, no activation of reporter expression was seen in the presence of Wy 14,643 upon cotransfection of PPARγ or PPARδ expression plasmids (FIG. 2). This lack of activation is unlikely to reflect differences in binding site specificity, as each of the PPAR isoforms bound efficiently to the AOX-PPRE as a heterodimer with RXR (as determined by gel mobility shift assays done using in vitro synthesized PPARα, PPARγ, and PPARδ, and/or RXRδ, and $^{32}$P-labeled AOX-PPRE oligonucleotide). Additional experiments revealed that overexpression of PPARγ and PPARδ interfered with the ability of PPARα to activate through the AOX-PPRE (FIG. 3). Thus, both PPARγ and PPARδ are expressed and can function as dominant repressors of PPARα-mediated responsiveness to Wy 14,643.

Figure 4:
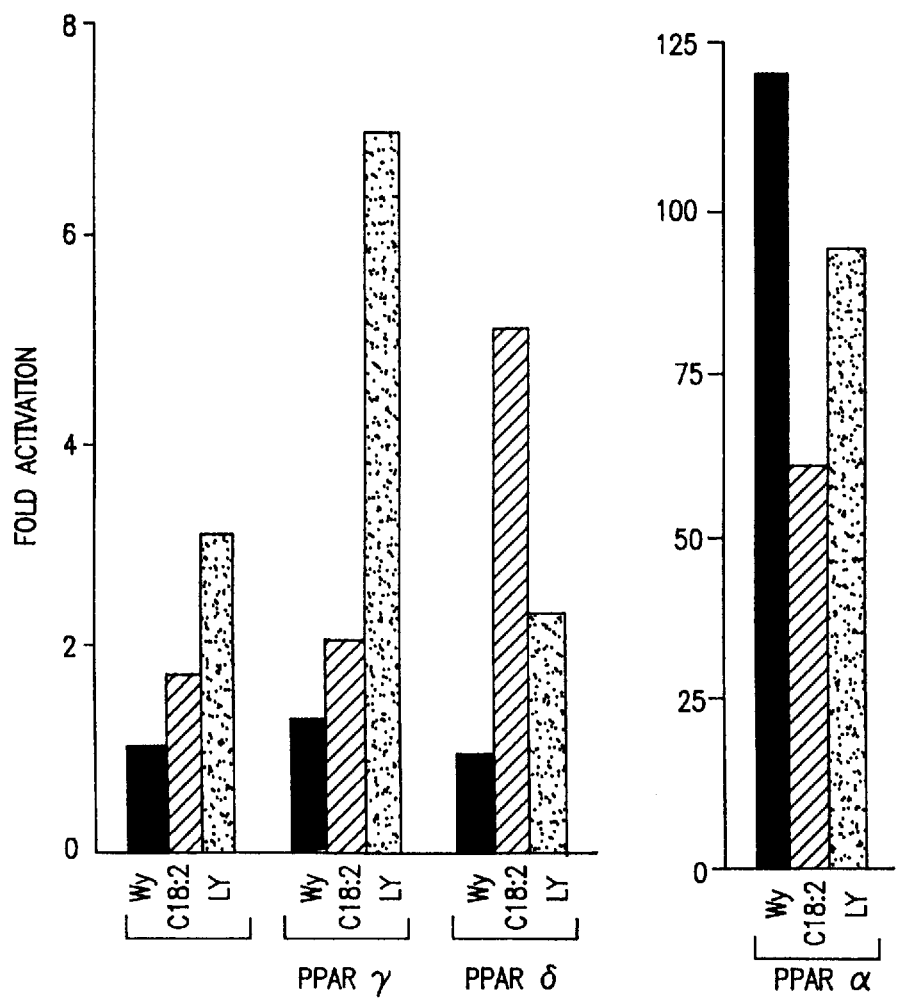

Since no activation of PPARγ and PPARδ was detected with Wy 14,643, other potential activators were tested, including a broad spectrum of peroxisome proliferators and fatty acids. As shown in FIG. 4, significant activation of PPARγ was obtained upon treatment with LY-171883, a leukotriene antagonist and peroxisome proliferator which lacks the carboxyl group typically found in this class of compounds (Foxworthy and Eacho, Biochem. Pharmacology 42:1487–1491 (1991)). Conversely, no activation of PPARγ was seen in the presence of linoleic acid (FIG. 4).

In contrast to the results obtained with PPARγ, PPARδ was activated in the presence of linoleic acid, but was not activated upon treatment with LY-171883. Both LY-171883 and linoleic acid are strong activators of PPARδ (FIG. 4). Interestingly, each of the three PPAR isoforms was activated with a distinct rank order of efficacy by these compounds:
PPARα: Wy 14,643>LY-171883>linoleic acid;
PPARγ:
LY 171883>linoleic acid>Wy 14,643;
PPARδ:
linoleic acid>LY-171883 and Wy 14,643.
See FIG. 4. These data provide evidence that PPARγ and PPARδ can function as regulated activators of gene expression and that the three PPAR isoforms are pharmacologically distinct.

While the invention has been described in detail with reference to certain preferred embodiments thereof, it will be understood that modifications and variations are within the spirit and scope of that which is described and claimed.

That which is claimed is:

1. An isolated nucleic acid encoding an isolated mammalian peroxisome proliferator-activated receptor subunit protein of the γ subtype, or functional fragments thereof, wherein said fragments encode the DNA binding domain and/or the ligand binding domain of said protein, wherein said receptor, or funtional fragments thereof, have the ability to repress PPARα-mediated responses activated by Wy 14,643, wherein said receptor, or funtional fragments thereof, are characterized as being activated by LY-171883 but not linoleic acid, and wherein said nucleic acid hybridizes under high stringency conditions to a nucleic acid encoding the amino acid sequence set forth in SEO ID NO:2.

2. An isolated nucleic acid according to claim 1 having a contiguous nucleotide sequence that encodes the amino acid sequence set forth in SEQ ID NO:2 (PPAR-γ).

3. A vector comprising a nucleic acid according to claim 1.

4. A cell containing a vector according to claim 3.

5. A cell containing a nucleic acid according to claim 1.

6. A method for the recombinant production of a mammalian peroxisome proliferator-activated receptor (PPAR) comprising at least one PPAR subunit of the γ subtype, or functional fragments thereof, wherein said fragments encode the DNA binding domain and/or the ligand binding domain of said subunit, said method comprising expressing the nucleic acid of claim 1 in a suitable host cell, thereby producing said receptor.

7. A method according to claim 6, wherein said host cell is a CV-1 cell.

* * * * *